United States Patent [19]

Samyn

[11] Patent Number: 4,566,122
[45] Date of Patent: Jan. 21, 1986

[54] PROCESS AND APPARATUS FOR IDENTIFYING ARTICLES OF SHEET MATERIAL BY MEANS OF MICROWAVES

[76] Inventor: Johan Samyn, Oostnieuwkerksesteenweg 199, 8800 Roeselare, Belgium

[21] Appl. No.: 481,243

[22] Filed: Apr. 8, 1983

[30] Foreign Application Priority Data

Jul. 29, 1982 [LU] Luxembourg .......................... 84307

[51] Int. Cl.⁴ ....................... G06K 9/00; G01R 27/04
[52] U.S. Cl. .................................. 382/7; 324/58.5 R; 340/600; 382/58
[58] Field of Search ............... 209/534, 536, 576, 589; 250/271, 555–559, 562–563, 566, 571–572; 356/71–73; 343/5 PD; 427/7; 428/916; 340/673–675, 600; 235/439–440, 487, 491; 324/58.5 R, 58.5 A, 58.5 B; 162/146; 382/7, 58

[56] References Cited

U.S. PATENT DOCUMENTS

| | | | |
|---|---|---|---|
| 3,506,829 | 4/1970 | Hannan | 250/271 |
| 3,851,971 | 12/1974 | Koch | 356/398 |
| 4,183,989 | 1/1980 | Tooth | 428/916 |
| 4,265,703 | 5/1981 | Terliska | 162/146 |
| 4,352,988 | 10/1982 | Ishida | 250/559 |
| 4,368,421 | 1/1983 | Glander et al. | 324/58.5 A |
| 4,408,156 | 10/1983 | Veys | 324/58.5 R |

FOREIGN PATENT DOCUMENTS

| | | | |
|---|---|---|---|
| 2037755 | 2/1972 | Fed. Rep. of Germany | 356/71 |
| 2062854 | 5/1981 | United Kingdom | 209/534 |

Primary Examiner—Leo H. Boudreau
Attorney, Agent, or Firm—Shlesinger Arkwright Garvey & Fado

[57] ABSTRACT

An apparatus for the identification by microwaves of a sheet article composed of an electrically non-conductive material, the article being marked for identification by the incorporation therein of electrically conductive fibers. The apparatus comprises: at least two microwave emitter devices one adjacent the other; detectors of waves reflected by the article when advanced before said devices; a screen placed in front of at least one of the emitters; and, regulating means for raising the sensitivity of the identification signals by setting the distances between the emitter device, screen and support for the interposed article.

28 Claims, 4 Drawing Figures

FIG. 1
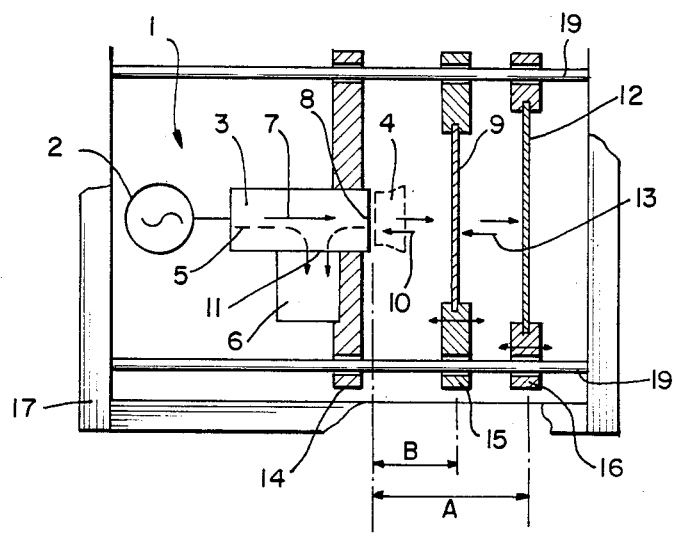
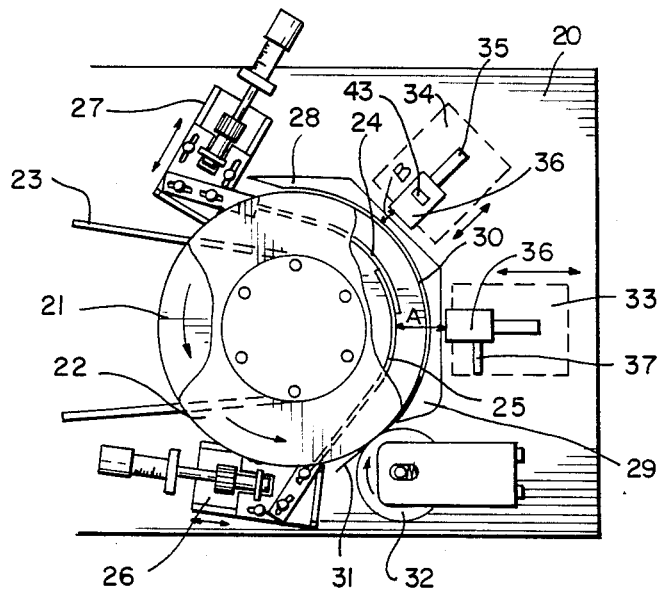
FIG. 2

PROCESS AND APPARATUS FOR IDENTIFYING ARTICLES OF SHEET MATERIAL BY MEANS OF MICROWAVES

This invention relates to a method and apparatus for identifying sheet or plate articles composed of electrically non-conducting materials by means of microwaves, the article being marked for identification by the incorporation of electrically conductive fibrous materials.

BACKGROUND OF THE INVENTION

One known method of marking sheet articles is to use, for example, paper sheets comprising small amounts of very thin metallic fibres distributed in the sheets and capable of absorbing and reflecting certain proportions of the energy of microwave radiation impinging on them. Therefore, it has been considered to apply this property to, among other things, certain types of security paper, such as banknotes, passports and bonds for their identification or verification of their authenticity by traversing them on a support through the path of a microwave emitter device and by detecting and measuring the proportion of the energy reflected and absorbed by the electrically conductive fibres embedded in the sheets. The amount of conductive fibres must remain small so as not to change too much the aspect and properties of the sheets or plates. It has been described in the French Patent Application No. 80,09095 of Applicant that fibres with smooth surfaces possessing a conductivity inferior to 10% of that of the standard of copper, with a diameter inferior to 50 μm and a length of less than 10 mm, produce an excellent microwave identification signal at quantities of e.g. 0.5% by weight in the article. These fibres produce a specific response which can hardly be imitated by other materials so that counterfeiting the marking is prevented. Moreover, it is generally desirable that the microwave detection device be very sensitive and capable of rapid response, and permit reproducible identifications of the same article.

BRIEF DESCRIPTION OF THE INVENTION

It is an object of the invention to provide a simple and compact apparatus for identifying the abovedescribed articles by detecting the waves reflected by the article when the microwaves released by at least two microwave devices, placed in front of the article, impinge on it. According to an important feature of the invention said microwave devices comprise an emitter, a circulator or a directional coupler in which a fraction of the reflected waves are deviated towards the detector. Apart from said microwave devices, the apparatus also comprises a reflecting screen placed in front of at least one said microwave device at a distance greater than the distance between this device and the article support. In order to raise (or at least optimize) the sensitivity of the identification signal it is necessary, according to the invention, to adjust the respective distances between the microwave device and the screen, and between the microwave device and the support, e.g. to position the screen and the support (or traversing means) with respect to said device. Therefore the apparatus also comprises means for adjusting the respective distances, e.g. the positioning of its component elements. Another specific object of the invention is to provide regulating methods for the apparatus, especially for positioning the elements.

According to a preferred embodiment, the apparatus may comprise various consecutive microwave devices with different polarization through whose path the article, carried by its support, is passed.

BRIEF DESCRIPTION OF THE DRAWINGS

The invention will now be described with reference to the adjoined drawings which refer to appropriate embodiments. At the same time, specific characteristics and advantages of the invention will be explained in greater detail.

FIG. 1 is a schematic view of the positioning of the basic elements of the apparatus;

FIG. 2 is a plan view of a continuously operating detection system comprising two microwave devices with different polarization;

DETAILED DESCRIPTION

Figure 3:
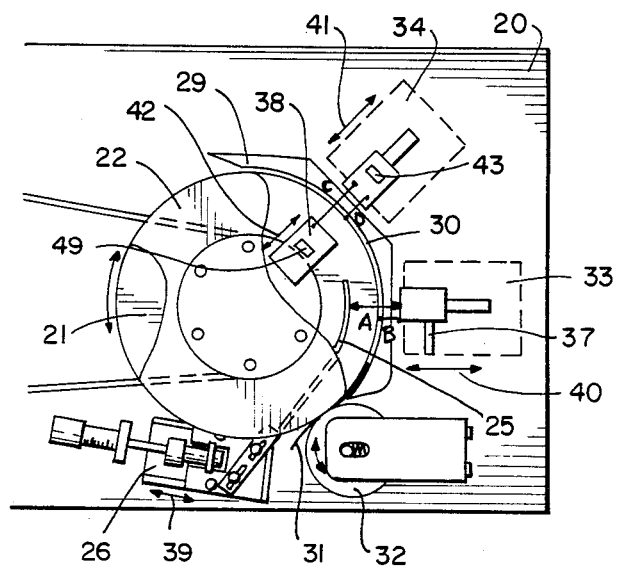
FIG. 3 is a view of a variant embodiment in which one of the screens is substituted by a detector for the waves transmitted by the article.

The apparatus according to FIG. 1 essentially comprises a microwave device 1. This device is composed of a microwave emitter 2 linked to a circulator 3 (to which an antenna 4 may be connected).

The emitter 2 may be a Gunn oscillator using a Gunn diode in a resonant cavity for producing microwaves with a frequency of more than 1 GHz, e.g. 25 GHz (wave length 12 mm). Oscillators of this type are commercially available. The output of the resonant cavity is connected with e.g. a ferrite circulator, commonly used in microwave transceivers for microwave reflection control systems. Such a circulator 3 is not ideal since a fraction 5 of the entering waves is deviated towards the detector 6 linked to the circulator. A plane polarized microwave beam 7 is emitted at port 8 of the circulator and launched against the sheet or plate article 9 placed with its surface perpendicular to the direction of the beam 7. A portion of the waves impinging on the article is reflected by it on account of the presence of electrically conducting fibrous material in the article and enters port 8 in the opposite direction. These reflected waves 10 are subsequently transmitted by port 11 of the circulator towards the detector 6 of the reflected waves. The detector 6 may be a known Schottky diode. Another fraction of the waves impinging on the article is transmitted and launched against the screen 12 composed of microwave reflecting material such as a metallic plate. The reflected waves 13 are partly transmitted by the article and this transmitted portion is added to the directly reflected waves 10 which enter port 8 in order to be captured by the detector 6. The elements 2, 3, 4 form the microwave device and the detector 6, respectively the article 9 and the screen 12 are supported in the respective frameworks 14, 15 and 16 which are adjustably mounted in a sliding manner on, for example, the bars 19 in a frame 17.

In A number of cases, for example in modern control systems and automatic banknote sorting devices, fairly compact microwave detection devices are needed. According to the invention it has become possible to design such a simple and compact system eliminating the horn antennae and detectors for the waves directly transmitted by the article as suggested in the French Patent Application No. 80.09095 of Applicant. The detector of these transmitted waves can be substituted, according to the invention, by a reflecting screen 12. This screen offers the further advantage that it shields the system against (sometimes variable) waves reflected by other objects surrounding the system since short distances between this screen and the detector are used, i.e. in the near field wave region. The use of high-frequency microwaves (for example 25 GHz) improves the sensitivity of the detection.

The use of non-ideal circulator 3 as described above also permits the creation of standing waves in the detector cavity. These waves are the result of a superposition of deviated waves 5 and reflected waves 10 and the creation of these standing waves makes it possible to produce a unique detection signal whose sensitivity can be regulated according to need. The regulating methods for the apparatus and for raising the sensitivity of the identification signal through the reflection of waves from the article are based on the phenomenon of these standing waves.

The apparatus is regulated as follows: first the distance A between the microwave device 1 and the screen 12 is adjusted in the absence of the article in order to obtain a predetermined reflection signal level in the detector 6 and the screen is fixed in this position by positioning (sliding) its support 16 on the bars 19. In fact, changing the distance A will cause a phase shift of the reflected waves 13 entering port 8 of the circulator as compared with the phase of the emitted waves. The superposition of the shifted waves 13 and the waves 5 will create a standing wave pattern as a function of the distance A. Therefore, for adjusting the distance A it is possible to fix (select) the level of the detected reflection signal which subsequently will serve as a reference level. If a minimum reflection signal level is preferred then it is possible to position the screen in such a manner that registration by the detector takes place in a knot of the standing wave. On the other hand, it is possible to choose a place for the screen where it produces a maximum reflection signal level coinciding with the peak of the standing waves.

When the distance A is determined and the screen fixed, then the distance B between the microwave device 1 and support 15 carrying article 9 is regulated (located between the microwave device and the screen) so that a reflection signal level is produced in the detector which is substantially different from that produced before (during regulating of the distance A); the support 15 is fixed in this position. The interposition of the article comprising the electrically conductive fibrous materials produces a still more complex signal composed of the direct reflections and the repeated reflections as well from the article and as from the screen (as described in general above). A fraction of the incident energy is reflected directly by the electrically conductive fibres embedded in the article; another fraction is transmitted to the article and launched against the screen which reflects this fraction of waves.

Another fraction is absorbed by the fibres. The fraction of the energy reflected by the screen impinges on its turn upon the article in the opposite direction (waves 13) and is divided once more into a fraction absorbed by the conductive fibres, a fraction transmitted towards the detector and a fraction in the form of repeated reflections towards the screen, and so on. The resulting wave 10 enters port 8 of the circulator and is added to wave 5. Nevertheless, the resulting wave will show a different shape and will be dephased with respect to that produced in the absence of the article between the microwave device and the screen. Moreover, a change in distance B will involve a supplementary shift of the phase of the resulting wave. Hence, it will be possible to adjust the distance B in such a manner as to register a signal level which shows a maximum difference with respect to the level registered in the absence of the article.

The apparatus shown in FIG. 2 concerns an example of the apparatus comprising traversing means for moving the article on its support. In general, this is the type of machine used for automatic continuous sorting for documents such as banknotes. In a frame 20 two parallel discs 21, 22 are mounted at a given distance apart on a shaft. This intermediate space comprises, on the one hand, the pulley moving the discs and put in motion by means of the belt 23, and, on the other hand, the metallic plates 24, 25 serving as reflection screens. The metallic plates 24, 25 are fixed by one of their ends in positioning elements 26, 27 having the form of, for example, micrometers mounted on the frame 20.

Opposite a portion of the circumferences of the disc 21, respectively 22, there are fixed elements 28, 29 with surfaces curved concentrically to the disc circumferences. The discs and these elements form a passage 30 for the documents 31 to be checked. The documents 31, comprising electrically conductive fibres, are introduced in the passage between the discs 21, 22 and a roller 32, and subsequently pushed forward in the path in front of the microwave devices 33, respectively 34. Each such device comprises an oscillator 35, a circulator 36 and a detector 37, respectively 43.

Nevertheless the polarization plane of the waves emitted by one of the devices 33, 34 is preferably essentially parallel to the direction of movement of the documents 31, while the polarization plane of the other device is essentially perpendicular to this direction.

EXAMPLE

A prototype of paper banknote 31 was prepared according to a process described in the French Patent Application No. 78.14617. Throughout the surface of the paper 4% by weight of stainless steel fibres with a diameter equivalent to 12 micron and a length of 5 mm are dispersed. In the course of the continuous manufacture of the paper on an industrial installation, the electrically conductive fibres were slightly oriented in the forward direction of the fresh layer of paper through the machine. This phenomenon seems to be characteristic for industrial paper fabrication and it is almost inimitable by manual or semi-industrial processes. The paper was cut into rectangular notes with the length of the rectangle parallel to the forward direction of the paper during manufacture. The note measured 18.5 cm to 7.5 cm. The note was introduced in the passage 30 around a disc drum 21, 22 of an automatic Crossfield sorting machine with a speed of 10 m/sec and the two detection signals were subsequently registered by the detectors 37 and 43 and compared. The oscillators 35 were of the type (Microwave Associates) MA 86790 and the circulators 36 were of the type MA 8K 221, while detectors 37, 43 with Shottky MA 86561 diodes were used. The rectangular ports 8 of the circulators had a length of 4.1 mm and a width of 2 mm. The polarization plane of the emitted waves was perpendicular to the length of the rectangular port. The emitted microwaves had a frequency of 25 GHz (wavelength 12 mm).

The distance A between the circulators 36 and the plates 24 and 25 was determined in the absence of the banknote by means of positioning micrometers 26, 27 so as to produce a minimum reference signal in the detectors 37, 43 corresponding to the knot in the standing wave produced at the detector ports. As soon as the distance A was known, the banknote to be checked was placed in its passage 30 right in front of the devices 33 and 34 and the distance B was determined so as to obtain a maximum signal in the detectors 37, 43. By respecting the predetermined distance A, the plates 24, resp. 25 and the devices 34, resp. 33 were shifted together in a direction perpendicular to that of the passage 30 into the position required for producing the maximum signal. This position corresponded with the desired distance B. As a result, the distance A was 25.5 mm and the distance B was 10.5 mm. The polarization plane of the waves emitted by the device 33 was parallel to the forward direction of the banknotes in the passage 30 (and hence parallel to the dominant orientation of the embedded electrically conductive fibres), whereas the polarization plane of the waves emitted by the device 34 was perpendicular to this forward direction.

Figure 4:
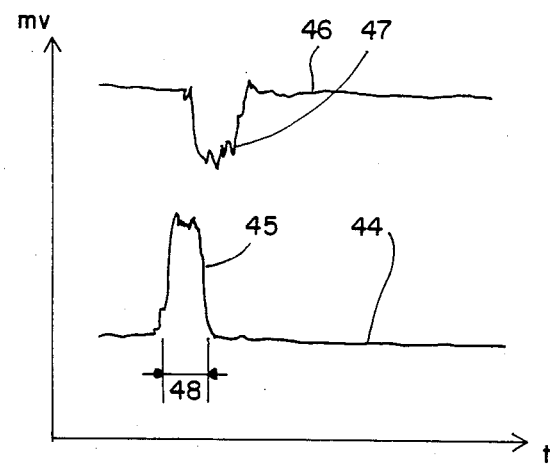
FIG. 4 shows the signals detected by a sheet comprising metallic fibres.

The signals received by the oscilloscope are shown in FIG. 4. The abscissa of this graph shows the time and the ordinate a measure proportional to the reflected energy. The line 44 shows the reflection signal registered by the detector 37 and the line 46 shows the reflection signal registered by the detector 43. It can be noticed immediately that the amplitude or the height of the peak 45 is higher than that of the peak 47 which indicates that there is a preferential orientation of the stainless steel fibres in the paper in the forward direction of the banknote 31 around the discs 21, 22. The peak 47 has been reversed in the drawing.

It is clear that the electrically conductive fibres oriented in the forward direction of the paper coincide with the polarization plane of the waves emitted by the first device 33 and hence cause (or at least contribute to) a high reflection level (i.e. an important signal or peak 45) in the detector 37.

On the contrary, when passing in front of the device 34, the fibres will reflect but very little of the energy launched onto them because the plane of polarization of the waves emitted by the device 34 is perpendicular to the direction of these fibres. A signal or peak 47 will therefore be much weaker, if not negligible, for these fibres. Nevertheless, in practice, the orientation of the fibres is more or less at random. Therefore, one may always expect a certain unnegligible signal 47 unless the fibres are forced in an appropriate direction during the manufacture of the article, for example, by means of magnets, when the fibres are magnetisable.

The width 48 of the peaks corresponds to a time interval of about 20 milliseconds which points to the exceptional aptitude of the apparatus to detect at a very high speed.

The invention relates also to an embodiment illustrated in the FIG. 3 which shows the very advantageous practical combination of at least two MW devices 33, 34 placed one adjacent to the other in an apparatus which further comprises a screen 25 placed in front of a first device 33 and a wave detector 38 for the transmitted waves placed in front of a second MW device 34. The support of the article 21, 22, 28, 29 is placed in front of the MW devices and between the devices 33, 34 and the screen 25, respectively the detector 38. The apparatus also comprises means for adjusting the respective distances between the different elements: i.e. the distances between any second device and any detector 38, any first device and any screen 25 and any first, resp. second devices and the support. The adjustment is indicated by the arrows 39, 40, 41 and 42.

In view of creating distinct signals permitting a better identification of the nature, dimensions and disposition of the electrically conductive fibres in the articles, it is advantageous to select the direction of the plane of polarization of the waves emitted by at least one of the first devices different from the direction of the plane of polarization of a second device. For example the plane of polarization of the wave from a first device may be parallel to the traversing direction of the article, whereas the plane of polarization of a second device may be perpendicular to this traversing direction.

Another possibility is to select the direction of the plane of the waves received by at least one of the detectors 38 different from that of the plane of polarization of the waves emitted by a second device 34 placed in front of these detectors. On the other hand, it may be preferable in certain cases that these two directions be parallel. If the directions of the plane of the waves received by a detector is selected different from that of the plane of polarization of the waves from a second device in front of the detector, it is preferable that these two planes cross at a 90-degree angle in order to create a maximum signal contrast in the respective detectors between the reflected waves and the waves transmitted to the detector. Either of the planes may then be chosen essentially parallel to the traversing direction of the article whereas the other is then perpendicular thereto.

If, on the contrary, the direction of the plane of received waves coincides with that of the plane of polarization of emitted waves opposite this detector 38, then these two planes may be oriented either parallel to the traversing direction of the article, or perpendicular to this direction.

A practical embodiment comprises for example a first device 33, emitting waves polarized in a plane parallel to the traversing direction or forward direction of the article 31 and a metallic screen 25 in front of this device. The waves emitted by a second device 34 will then have a plane of polarization oriented perpendicularly to the traversing direction of the article. The detector 38 in front of this device 34 will then be oriented so as to receive the full fraction of energy transmitted in the plane perpendicular to the forward direction of the article.

In another practical advantageous embodiment a first device 33, placed opposite the screen 25, will emit waves polarized in a plane perpendicular to the forward direction of the article. On the other hand, the detector 38 placed in front of the device 34 will be oriented so as to receive only the fraction of energy transmitted in a plane parallel to the forward direction of the article, whereas the plane of polarization of the waves emitted by the device 34 will also be oriented parallel to this traversing direction.

In order to regulate the respective desirable orientations of the planes of polarization of the waves emitted by the different devices, as well as of the waves transmitted to the detectors, the apparatus will, in general comprise conventional and non-illustrated means for adjusting the angular position of rotation of the devices and/or detectors about an axis parallel to the direction of propagation of the emitted waves.

The regulation will now be described of an apparatus comprising a combination of at least two wave devices 33 resp. 34, one adjacent to the other, a screen 25 placed in front of one of the first devices 33 and a wave detector 38 placed in front of the second devices 34 with a support 21, 22, 29 for the article 31 placed between these elements. This adjustment, i.e. the position of the elements, aims at raising the sensitivity of the identification signal. In general, first the distance A between a first device 33 and the screen 25 is regulated in the absence of the article 31 so as to obtain in the detector 37 a predetermined reflection signal level and the screen 25 is fixed in this position. Next the distance B between a first device 33 and the support 21, 22, 29 of the article is regulated while this support carrying the article 31 is located between this device and the screen placed in front of it so as to obtain that in the detector 37 a reflection signal level is produced substantially different from that obtained during the absence of the article and the support is fixed in this position.

Next the distance C between a second device 34 and the detector 38 is regulated in the absence of the article so as to obtain in this detector a predetermined level of the transmission signal and this distance C is readjusted in the absence of the article by a small displacement so as to obtain a predetermined reflection signal level in a second detector 43. The detector 38 and the device 34 are fixed this distance apart. Finally, after having placed the article 31 in the passage 30 of the support between the detector 38 and the device 34, the distance D between said device 34 and the support carrying the article 31 is regulated so as to obtain in the detector 43 a reflection signal level substantially different from that produced in the absence of the article and the support is fixed in this position.

The distance A can be regulated and the screen 25 fixed so as to produce, as desired, either a minimal signal or a maximum signal in the detector 37. Anyway it will be advantageous to fix the article 31 in its support in a position so as to obtain in the detector 37 a reflection signal level offering a maximum difference with respect to the level registered in the absence of the article.

For regulating the distance C account is taken of the fact that the presence of the metallic detector 38 makes that a portion of the waves emitted by the device 34 are reflected by the metallic parts of the detector. The same superposition of emitted and reflected waves (with different phases) produces a standing wave. By changing the distance C one can select the level of the registered transmission signal in the detector 49. This detector 49 is of the same type as that (43) fixed to the device 34. Preferably the distance C will be taken so as to obtain a maximum level for the transmission signal. By readjusting the distance C the detector 38 or the device 34 will preferably be shifted over a small distance so as to produce a minimum reflection signal level in the detector 43. This reflection signal is considered hereafter as reference reflection signal. A supplementary effect of the readjustment is that the predetermined maximum transmission level (at distance C) has diminished slightly. The level of the registered transmission signal in the detector 49 at this readjusted distance is considered as reference transmission signal.

Finally, the article 31 is placed in the support 21, 22, 29 between the detector 38 and the device 34 and the distance D between the device 34 and the article is regulated (thereby respecting the readjusted distance C between the device 34 and the detector 38) so as to obtain in the detector 43 a maximum reflection signal level. The interposition of the article 31 between the device 34 and, analogous to what has been described above, the detector 38 creates superposition phenomena having the form of a complex of direct waves, reflected waves and waves transmitted at different phases. The result of the superposition produces a standing wave which allows to fix the reflection signal level as a function of the distance D.

Although the invention has been described with reference to the apparatus shown in the Figures, it must be understood that it is not limited to these embodiments. The frequency of the microwaves may differ from one MW device to another. A first device may, for example, operate at 25 GHz and a second one, for example, at 10 GHz. A higher frequency implies a more accurate and delicate positioning since the wave length of standing waves is half that of the emitted waves. Instead of traversing the article subsequently in the path of two MW devices, one may conceive, for example, to pass it twice through the path of the same device by changing between both passages either the orientation of the article, or the orientation of the plane of polarization of this device.

It is also evident that the detection signal may produce a command through the intervention of a relay or other actuator in order to eliminate from a continuous series of examined articles those which do not correspond with the set standards. In the parctice of automatic sorting of banknotes, for example, this measure would permit to eliminate counterfeited banknotes automatically.

The sheet or plate articles may either be fibrous structures such as paper, non-woven articles, fabrics, yarns, or non-fibrous structures, for example based on plastic or ceramic materials, or laminated combinations of these structures. During manufacture they may be marked locally only by the local embedment of electrically conductive fibrous materials.

The use of fibrous materials, other than the BEKINOX ® stainless steel fibres of Applicant, is possible. Nevertheless, the electrical conductivity of Bekinox ® fibres is almost ideal for the identification system according to the invention since it offers absorption and reflection characteristics of the same order of magnitude. Hence, these values may be detected by the same type of detectors. Moreover, the small diameter offers a maximum absorption capacity in the detection circumstances according to the invention, e.g. by selecting a good combination of geometry and (low) concentration of the fibres as a function of the frequency of the MW devices. The small diameter of the fibres also favours the aspect of the article, e.g. security paper. A regular surface of the fibres avoids variations in the detection signal.

By using the fibres with fairly high conductivity and by respecting the fibre dimensions (diameter under 25 micron, length under 10 mm) as well as the order of magnitude of the concentration of these fibres in the article (less than 5% by weight), the articles will offer absorption values that are too weak and reflection values that are too high so that they can no longer be distinguished from plates or metallic layers with the system according to the invention.

On the other hand, by using fibres with a very weak conductivity, (lower than that of BEKINOX ® fibres) it will be necessary to incorporate thicker fibres (in order to reach an unnegligible absorption level) which would deteriorate the aspect of the article.

If the surface of the articles is fairly large and the marking, for example, limited to limited places in the surface, it is evident that various combinations of transceivers (screen, resp. wave detectors) must be mounted in the apparatus one next to the other in order to permit a proper examination of the entire surface.

All these variants as well as others known to anyone skilled in the art are considered to be part of the invention and covered by the following claims.

I claim:

1. An apparatus for the identification of a sheet or article composed of an electrically non-conductive material, the article being marked for the identification, by the incorporation of electrically conductive materials comprising: a frame; at least two microwave devices, one adjacent the other, mounted in said frame; a support, for the article, placed in front of said microwave devices; at least two detectors for waves reflected by the article when the article is advanced before said devices, the article thereby traversing each said detector and respective device in a traversing direction; a circulator means or directional coupler means, associated with each said microwave devices, for deviating waves reflected by the article towards said detectors; a screen means, for reflecting waves, positioned in front of at least one of the microwave devices at a distance greater than that between said microwave device and said support; and, adjusting means for adjusting the respective distances between said microwave device and said screen and said microwave device and said support.

2. An apparatus according to claim 1, comprising in addition traversing means for moving the article carried by the support.

3. An apparatus according to claim 1, wherein the plane of polarization of the waves emitted by at least one device being different from the plane of polarization of the waves emitted by an other one.

4. Apparatus according to claim 3, whereby the plane of polarization of the waves emitted by one of the devices is essentially parallel to the direction of the movement of the article, while the plane of polarization of an other device is essentially perpendicular to that direction.

5. Apparatus according to claim 1, comprising at least two microwave devices, one adjacent the other, a screen placed in front of at least one first device and a detector for the transmitted waves placed in front of at least one second device at a greater distance than that between said second device and the support of the article, as well as adjusting means for adjusting the respective distances between said first device and the screen and between said second device and said detector, and between the support and the microwave devices.

6. An apparatus according to claim 5, whereby the plane of polarization of the waves emitted by at least one of the first devices has a direction different from that of the plane of polarization of a second device.

7. An apparatus according to claim 6, wherein the plane of polarization of the waves emitted by at least one of the first devices is essentially parallel to the traversing direction of the article while the plane of polarization of at least one of the second devices is essentially perpendicular to this direction.

8. An apparatus according to claim 5, wherein the direction of the plane of the waves received by at least one of said detectors, is different from that of the plane of polarization of the waves emitted by a second device placed in front of these detectors.

9. An apparatus according to claim 8 whereby the plane of the waves received is essentially parallel to the traversing direction of the article, while the plane of polarization of the waves emitted by a second device placed in front of the detector is essentially perpendicular to this traversing direction.

10. An apparatus according to claim 8 whereby the plane of polarization of the waves emitted by a second emitter is essentially parallel to the traversing direction of the article, while the plane of the received waves is essentially perpendicular to this direction.

11. An apparatus according to claim 5, wherein the plane of the waves received by at least one of the detectors is parallel to the plane of polarization of the waves emitted by a second device placed in front of these detectors.

12. An apparatus according to claim 11 whereby the direction of the plane of the received waves is essentially parallel to the traversing direction of the article.

13. An apparatus according to claim 12 whereby the plane of polarization of the waves emitted by a first emitter placed in front of the reflection screen is perpendicular to the traversing direction of the article.

14. An apparatus according to claim 11 whereby the direction of the plane of received waves is essentially perpendicular to the traversing direction of the article.

15. An apparatus according to claim 14 whereby the plane of polarization of the waves emitted by a first emitter placed in front of the reflection screen is parallel to the traversing direction of the article.

16. An apparatus according to claim 1, comprising: adjusting means for the angular position of rotation of the emitters and/or detectors around an axis parallel to the direction of propagation of the emitted waves.

17. An apparatus according to claim 1 further comprising actuator means for responding to the identification signals produced by the detectors of waves for eliminating the non-standarized sheet articles in a continuous series of examined articles.

18. A method for regulating, an apparatus for the identification of a sheet or plate article, the article composed of an electically non-conductive material and being marked for the identification by the incorporation of electrically conductive materials, the apparatus including one first and at least one second microwave device for producing waves, at least one first and one second detector of waves, a support for the article, a screen means for reflecting waves and means for adjusting respective distances between said microwave device and said screen and also said microwave device and said support, comprising the steps of:

(a) regulating the distance A between the microwave devices and the screen in the absence of the article so as to obtain in the detector a predetermined reflection signal level;
(b) fixing the distance A between the microwave devices and the screen;
(c) regulating the distance B between the device and the article support while the support carrying the article is located between said device and the screen in order to produce in the detector a reflection signal level substantially different from that produced by regulating the distance A; and,
(d) fixing the distance B between the device and the article support.

19. A regulating method according to claim 18, whereby the screen is fixed in a position so as to obtain a minimal signal in the detector.

20. A regulating method according to claim 18, whereby the screen is fixed in a position so as to obtain a maximal signal in the detector.

21. A regulating method according to claim 18 whereby the article support is fixed in a position so as to obtain a signal level in the detector showing a maximum difference with respect to the signal level obtained in the absence of the article.

22. A method for regulating an apparatus for the identification of a sheet or plate article, the article composed of an electrically non-conductive material, the article being marked for the identification by the incorporation of electrically conductive materials, the apparatus including one first and at least one second microwave device for producing waves, at least one first and one second detector of reflected waves, at least one detector of transmitted waves, a support for the article, and a screen for reflecting waves, comprising the steps of:
  (a) regulating the distance A between a first microwave device and a screen in the absence of the article so as to obtain in a first detector for the waves a predetermined reflection signal level;
  (b) fixing the distance A between a first microwave device and a screen;
  (c) regulating the distance B between the device and the article support, while said support carrying the article is located between said device and said screen so as to obtain in said reflector a reflection signal level substantially different from that obtained by fixing the distance A;
  (d) fixing the distance B between the device and the article support;
  (e) regulating the distance C between a second microwave device and a detector for the transmitted waves in the absence of the article so as to obtain in said detector a predetermined transmission signal level;
  (f) readjusting the distance C in the absence of the article so as to obtain in a second detector of reflected waves a predetermined reflection signal level;
  (g) fixing the distance C to a readjusted position;
  (h) fixing the article in the support between the detector for the transmitted waves and the second device;
  (i) regulating the distance D between the second device and the support carrying the article so as to obtain in the second detector for the reflected waves a reflection signal level substantially different from that obtained by readjusting the distance C; and,
  (j) fixing the distance D between the second device and the support carrying the article.

23. A regulating method according to claim 22 whereby the screen is fixed in a position so as to obtain a minimal signal in the first detector for the reflected waves.

24. A regulating method according to claim 22 whereby the screen is fixed in this position so as to obtain a maximal signal in the first detector for the reflected waves.

25. A regulating method according to claim 22, whereby the support of the article is fixed in a position so as to obtain in said first detector a reflection signal level showing a maximal difference compared with the signal level obtained in the absence of the article.

26. A regulating method according to claim 22 wherein the distance C is regulated so as to obtain in the detector for the transmitted waves a maximal transmission signal level.

27. A regulating method according to claim 22 whereby the distance C is readjusted so as to obtain a minimum reflection signal level in said second detector.

28. A regulating method according to claim 27, whereby the distance D is regulated so as to obtain in said second detector a maximum reflection signal level.

* * * * *

UNITED STATES PATENT AND TRADEMARK OFFICE
CERTIFICATE OF CORRECTION

PATENT NO. : 4,566,122
DATED : January 21, 1986
INVENTOR(S) : Johan Samyn

It is certified that error appears in the above-identified patent and that said Letters Patent is hereby corrected as shown below:

On the title page, the assignee should read

-- N.V. Bekaert, S. A.,

Zwevegem, Belgium --.

Signed and Sealed this

Fifteenth Day of April 1986

[SEAL]

Attest:

DONALD J. QUIGG

Attesting Officer

Commissioner of Patents and Trademarks